United States Patent
Schmidt et al.

(10) Patent No.: US 6,932,797 B2
(45) Date of Patent: Aug. 23, 2005

(54) LIQUID REMOVAL SYSTEM WHICH IS COMPRESSIBLE IN THE LONGITUDINAL AND/OR IN THE TRANSVERSE DIRECTION

(75) Inventors: Mattias Schmidt, Idstein (DE); Bruno Hohannes Ehrnsperger, Frankfurt/M. (DE)

(73) Assignee: The Procter & Gamble Company, Cincinnati, OH (US)

( * ) Notice: Subject to any disclaimer, the term of this patent is extended or adjusted under 35 U.S.C. 154(b) by 210 days.

(21) Appl. No.: 10/168,879

(22) PCT Filed: Dec. 20, 2000

(86) PCT No.: PCT/US00/34865

§ 371 (c)(1),
(2), (4) Date: Jun. 21, 2002

(87) PCT Pub. No.: WO01/45603

PCT Pub. Date: Jun. 28, 2001

(65) Prior Publication Data

US 2003/0010700 A1 Jan. 16, 2003

(30) Foreign Application Priority Data

Dec. 23, 1999 (EP) .............................. 99125933

(51) Int. Cl.⁷ .............................................. A61M 1/00
(52) U.S. Cl. ................. 604/327; 604/313; 604/540
(58) Field of Search ................ 604/313, 319–321, 604/327, 355, 540

(56) References Cited

U.S. PATENT DOCUMENTS 4,525,166 A * 6/1985 Leclerc ...................... 604/133
4,636,207 A * 1/1987 Buell .......................... 604/370
4,886,508 A * 12/1989 Washington ................. 604/327
5,295,983 A * 3/1994 Kubo .......................... 604/329
5,562,646 A 10/1996 Goldman et al.
5,599,335 A 2/1997 Goldman et al.
5,678,564 A 10/1997 Lawrence et al.
5,911,222 A 6/1999 Lawrence et al.
6,160,198 A * 12/2000 Roe et al. .................... 604/361
6,186,991 B1 * 2/2001 Roe et al. .................... 604/361
6,394,988 B1 * 5/2002 Hashimoto .................. 604/355
6,537,262 B2 * 3/2003 Thompson .................. 604/347
6,554,817 B1 * 4/2003 Oki et al. .................... 604/393
6,641,567 B1 * 11/2003 Williams .................... 604/327
6,663,610 B1 * 12/2003 Thompson et al. ......... 604/313
2002/0087131 A1 * 7/2002 Wolff et al. ................. 604/319

FOREIGN PATENT DOCUMENTS

| WO | WO 94/13704 A1 | 6/1994 |
|---|---|---|
| WO | WO 00/00129 A1 | 1/2000 |
| WO | WO 00/00136 A1 | 1/2000 |
| WO | WO 00/00138 A1 | 1/2000 |
| WO | WO 00/00143 A2 | 1/2000 |
| WO | WO 00/00146 A2 | 1/2000 |

* cited by examiner

*Primary Examiner*—Larry I. Schwartz
*Assistant Examiner*—Michael G. Bogart
(74) *Attorney, Agent, or Firm*—Edward J. Milbrada; Dara M. Kendall; Ken K. Patel

(57) ABSTRACT

The present invention provides a liquid removal system for applications where there is a need for liquid removal including laboratories and workshops as well as medical applications as well as dental applications. The liquid removal system exhibits improved wearing comfort by comprising an interface device which is compressible in the longitudinal and/or transverse dimension.

8 Claims, 1 Drawing Sheet

LIQUID REMOVAL SYSTEM WHICH IS COMPRESSIBLE IN THE LONGITUDINAL AND/OR IN THE TRANSVERSE DIRECTION

FIELD OF THE INVENTION

The present invention provides a liquid removal system for applications where there is a need for liquid removal including laboratories and workshops as well as medical applications as well as dental applications.

BACKGROUND

Articles to manage body exudates such as urine are well known in the art. In this context, managing body exudates includes acquiring, distributing, and storing body exudates such as urine, menses fecal material, and the like. A wide variety of article has been proposed including diapers, sanitary napkins, adult incontinence articles such as briefs or bed mats, underarm sweat pants, catheters, bottles, bed pans, and the like.

In U.S. Pat. No. 5,678,564 (Lawrence et al.) and U.S. Pat. No. 5,911,222 (Lawrence et al.) a liquid removal system having an interface device and a vacuum source is described. The interface device has a porous membrane with an entrance zone on one side. The vacuum source maintains a vacuum on the side of the membrane opposite the entrance zone when the membrane is wetted. Liquid which contacts the wetted porous membrane is removed from the interface device by the vacuum source. Whilst this device is capable of acquiring and transporting urine, this liquid removal system comprises a plastic shell which is only capable to conform to minor differences in the physique of a patient. In particular for mobile patients, it is however desirable to provide a liquid removal system which readily adapts to the movements of the patient by being compressible in the longitudinal and/or in the transverse direction.

Hence, it is an object the present invention to overcome the problems posed by the liquid removal systems of the prior art.

It is a further object of the present invention to provide a liquid removal system which is compressible in the longitudinal and/or in the transverse direction.

SUMMARY OF THE INVENTION

The liquid removal system of the present invention comprises an interface device. The interface device is intended to acquire the body liquid from the wearer and accordingly is intended to be worn close to the urethra exit of the wearer. The interface device comprises a first zone, a second zone, and a porous membrane separating the first zone from the second zone. The second zone is adapted to be connected to a suction source and a porous membrane is capable of maintaining a suction in the second zone without permitting air from the first zone to pass through the membrane into the second zone when the membrane has been wetted with a first liquid. A second liquid is removed from the first zone by the suction in the second zone upon entering the first zone and contacting the porous membrane by passing through the membrane into the second zone. The first zone of the liquid removal system of the present invention has the user facing surface and the second zone has a back surface. The liquid removal system of the present invention is characterized in that its interface device is compressible in the longitudinal direction and/or is compressible in the transverse direction.

DETAILED DESCRIPTION OF THE DRAWINGS

Figure 1:
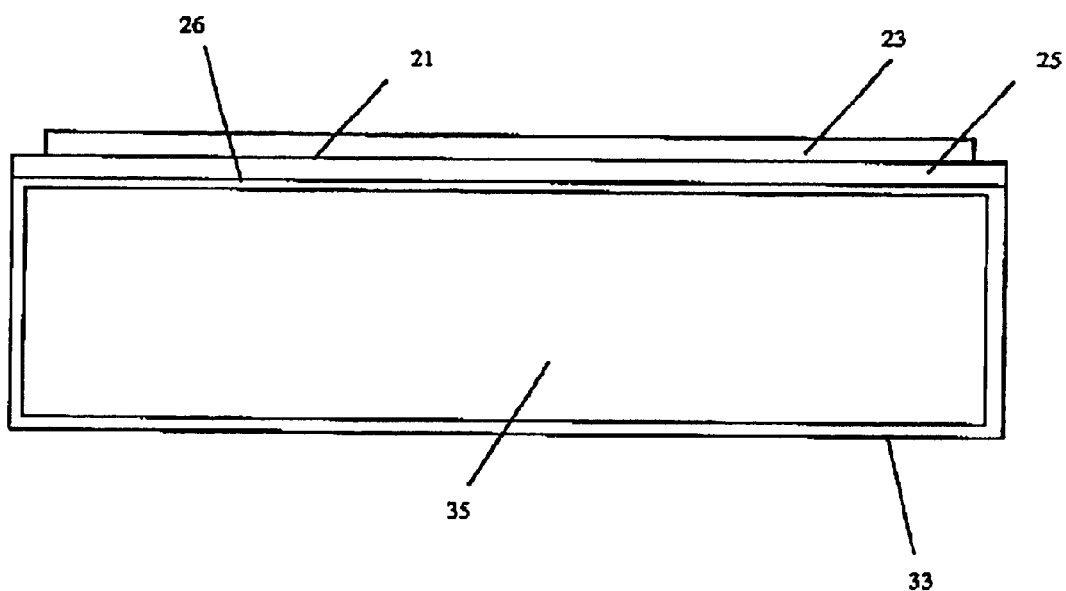
FIG. 1 shows a plan view of the absorbent article of the present invention.

FIG. 1 illustrates a liquid removal system of the present invention. The system comprises a first zone 25, a second zone 35, a user facing surface 21 of the first zone, a garment facing surface 26, and a porous membrane 33.

DETAILED DESCRIPTION OF THE INVENTION

Materials suitable for the membrane of the present invention and suction sources suitable for the liquid removal system of the present invention are described for example in U.S. Pat. No. 5,678,564 (Lawrence et al.) U.S. Pat. No. 5,911,222 (Lawrence et al.) incorporated herein by reference. Preferably, the membrane material can be bend to an extent which includes most of the typical in-use conditions without substantially loosing its functionality. More preferably, the membrane material of the present invention has a low bending moment along at least one of the two major axis of its major surfaces in order to improve the comfort of the system. Preferably, the suction source as a whole or at least those parts connecting the suction source with the second zone of the liquid removal system are chosen to be flexible and/or compressible in order to improve the comfort of the system.

For the purpose of the present invention, a locally Cartesian coordinate system is defined relative to the liquid removal system and its positioning relative to the wearer during use. The longitudinal or x--direction is defined as the direction running from the front waist region of the wearer to the back waist region of the web. Typically, the longitudinal direction is the longest dimension of the liquid removal system. The transverse or y--direction is defined as direction running from the left side of the wearer to the right side of the wearer. The z--direction is normal to the x--direction and to the y--direction and accordingly is also substantially normal to the body surface of the wearer during use. It is to be understood in this context that during wear of the liquid removal system of the present invention the liquid removal system conforms to the body shape of the wearer and that accordingly the coordinate axis at the front region of the liquid removal system may not coincide with the coordinate axis in the back region of the liquid removal system.

The liquid removal system of the present invention is compressible either in the longitudinal direction or in the transverse direction. It may also be compressible in longitudinal direction as well as in the transverse direction. The term "compressible" as used herein refers to liquid removal systems which change their longitudinal and/or transverse dimension as a result of a relatively low external pressure or force exerted onto liquid removal system in that direction. This compressibility leads to increased comfort during wear of the liquid removal system since the compressibility of the liquid removal system allows the liquid removal system to adapt to the changing body shape of the wearer. Substantial changes of the body shape of the wearer are present for mobile patients as well as for bed ridden patients. Preferably, the liquid removal system of the present invention is compressible in the respective direction to less than 90 percent of its original dimension in that direction under a compressive pressure of 10 kPa, more preferably to less than 80 percent of its original dimension in that direction, most preferably to less than 60 percent of its original dimension in that direction.

The user facing surface of the first zone of the liquid removal system of the present invention is intended to be worn adjacent to the body surface of the wearer in proximity to the urethra exit. The user facing surface comprises a urine acquisition zone which may coincide with the surface dimensions of the total user facing surface of the liquid removal system or which may be covering only a portion of the user facing surface. At least the urine acquisition zone of the user facing surface may be covered by soft, hydrophobic topsheet. For improved comfort, the topsheet material may be chosen to have a low bending moment in the longitudinal and/or transverse direction. Materials suitable for the topsheet of the present invention include but are not limited to woven and nonwoven materials comprising natural fibers, synthetic fibers, or combinations thereof. A preferred to topsheet material is a carded nonwoven web material. More preferably, the carded nonwoven web material comprises crimped staple fibers. Furthermore, the topsheet material may be a high bulk nonwoven web material.

The second zone may comprise a flexible support means and may be enveloped by a flexible, liquid impermeable material. A wide variety of flexible support means are known in the art such as for example open cell, polymeric foams or framework structures made from synthetic polymeric material. Additionally, a wide variety of suitable liquid impermeable materials is known in the art such as for example films of polymeric material, nonwoven web material, and the like. For improved comfort, the backsheet material may be chosen to have a low bending moment in the longitudinal and/or transverse direction. Further, the backsheet material may be covered by a fibrous, for example nonwoven, material to improve the tactile feel of its outer surface. The flexible support means may be compressible in the longitudinal and/or in the transverse direction. Preferably, the flexible support means is compressible in the longitudinal and/or transverse direction to less than 90 percent of its original dimension in that direction, more preferably to less than 80 percent of its original dimension that direction, most preferably to less than 60 percent of its original dimension in that direction under a compressive pressure of 10 kPa. The flexible support means of the present invention may comprise a plurality of substantially incompressible elements. It is to be understood in this context that these substantially incompressible elements must not fill up all a void volume inside the second zone of the liquid removal system in order to allow the second liquid to be transported away from the membrane. For example, the substantially incompressible elements may be spheres, Raschig rings, Pearl saddles. At least a portion of the substantially incompressible element may be free movable inside the second zone in order to improve compress ability while still maintaining the overall volume of the second zone.

The user facing surface of the liquid removal system may comprise an external dam to see of the device to the wearer thereby preventing leakage of urine. The external dam may comprise a liquid impermeable nonwoven barrier cuff such as those well known from disposable absorbent articles. Such a barrier cuff may comprise elastification means in order to improve conformity with the body of the wearer during use. Preferably, the barrier cuff of the present invention is vapor permeable to improve the breathability of the liquid removal system.

The liquid removal system of the present invention may comprise an alignment means which aligns the urine acquisition zone with the exit of the urethra of the wearer. The alignment means may comprise a member disposed onto the user facing surface which is shaped according to the body surface of the wearer in order to impede excessive movement of the liquid removal system relative to the body of the wearer during use. In particular for male patients, the alignment means may align the urine acquisition zone with the distal end of the penis of the wearer such as by mechanical means limiting the movement of the penis relative to the urine acquisition zone.

As is readily apparent to the skilled person, the comfort improvements can only be achieved by providing a liquid removal system exhibiting a sufficient performance for example in terms of acquisition rate, liquid transportation rate, storage capacity, membrane performance, and the like.

In the following, a suitable embodiment of the liquid removal system and of suitable members for a liquid removal system respectively will be described. The liquid removal system is assembled from an open celled foam material which is completely enveloped by a membrane. A suitable membrane material is available from SEFAR of Rüschlikon, Switzerland, under the designation SEFAR 03-20/14. A suitable foam material is available from Recticel of Brussels, Belgium, under the designation Bulpren S10 black. A suitable technique to completely envelope the foam material with the membrane material is to wrap the membrane material around the foam material and to subsequently heat seal all open edges of the membrane material. It will be readily apparent to the skilled practitioner to choose other similarly suitable materials. Depending on the specific intended application of the liquid removal system, it may also be required to choose similar materials with slightly different properties. After assembly, the liquid removal system is activated by immersing the liquid removal system in water or in synthetic urine until the liquid removal system is completely filled with liquid and until the membranes are completely wetted with liquid. After activation, a part of the liquid inside the liquid removal system may be squeezed out by applying an external pressure to the liquid removal system. If the activation of the liquid removal system was successful, the liquid removal system will not suck air through the membranes.

The particular geometry of the liquid removal system of the present invention can be varied to according to the specific requirements off the intended application. If, for example, the liquid removal system is intended to be used in an absorbent article the liquid removal system may be defined such that its zone of intended liquid acquisition fits between the legs of the wearer and further that its intended liquid discharge zone matches the form of the storage member associated to it. Accordingly, the outer dimensions of the liquid removal system such as length, width, or thickness may also be adapted to the specific needs of the intended application. In this context, it has to be understood, however, that the design of the outer form of the liquid removal system may have an impact on its performance. For example, certain cross sections of the liquid removal system directly impact on its flow rate.

For application of the liquid removal system in an absorbent article according to the present invention, the liquid removal system is combined with a storage member. The term "liquid storage member" refers to a member which is capable of receiving and storing liquid. The volume of the liquid storage member may vary with the amount of stored liquid such as by swelling. Typically, the storage member will imbibe the liquid by means of capillary suction and/or osmotic pressure. Other storage members may also use vacuum as a means to store the liquid. The liquid storage member is further capable of holding at least a portion of the stored liquid under external compressive pressure. Suitable storage members are well known in the art and may comprise for example a super absorbent polymeric material such as polyacrylate. The storage member may further comprise a fibrous structure, such as a pad of cellulosic fibers, in which the particulate superabsorbent material is dispersed. In order to pick up the liquid discharged from the liquid removal system, the storage member may be placed in direct liquid communication with the intended liquid discharge zone of the liquid removal system. A suitable storage member is for example a superabsorbent polymer such as available from CHEMDAL, United Kingdom, under the designation ASAP400.

Further examples of suitable superabsorbent polymers, often also referred to as "hydrogel forming polymer" or "absorbent gelling material", are described in U.S. Pat. No. 5,562,646 (Goldman et al.), issued Oct. 8, 1996 and U.S. Pat. No. , 5,599,335 (Goldman et al.), issued Feb. 4, 1997.

Other liquid removal systems suitable for the purposes of the present invention are described for example in the PCT patent application No. PCT/US98/13497 entitled "Liquid transport member for high flux rates between two port regions" filed in the name of Ehrnsperger et al. filed on Jun. 29, 1998, and in the following PCT patent applications PCT/US99/14796 entitled "High flux liquid transport members comprising two different permeability regions" (P&G case CM1840MQ) filed in the name of Ehrnsperger et al., PCT/US99/14654 entitled "Liquid transport member for high flux rates between two port regions" (P&G case CM1841MQ) filed in the name of Ehrnsperger et al., PCT/US99/14638 entitled "Liquid transport member for high flux rates against gravity" (P&G case CM1842MQ) filed in the name of Ehrnsperger et al., PCT/US99/14633 entitled "Liquid transport member having high permeability bulk regions and high bubble point pressure port regions" (P&G case CM1843MQ) filed in the name of Ehrnsperger et al. All of these documents are enclosed herein by reference.

In one embodiment of the present invention, the liquid removal system of the present invention is geometrically saturated or substantially geometrically saturated with free liquid. The term "free liquid" as used herein refers to liquid which is not bound to a specific surface or other entity. Free liquid can be distinguished from bound liquid by measuring the proton spin relaxation time T2 of the liquid molecules a according to NMR (nuclear magnetic resonance) spectroscopy methods well known in the art.

The term "geometrically saturated" as used herein refers to a region of a porous material in which the liquid accessible void spaces have been filled with a liquid. The void spaces referred to in this definition are those which are present in the current geometric configuration of the porous material. In other words, a geometrically saturated device may still be able to accept additional liquid by and only by changing its geometric configuration for example by swelling, although all voids of the device are filled with liquid in the current geometric configuration. A device for handling liquids is called geometrically saturated, if all porous materials that are part of the device and intended for liquid handling are geometrically saturated.

The term "porous material" as used herein refers to materials that comprise at least two phases a solid material and a gas or void phase—and optionally a third liquid phase that may be partially or completely filling said void spaces. The porosity of a material is defined as the ratio between the void volume and the total volume of the material, measured when the material is not filled with liquid. Non-limiting examples for porous materials are foams such as polyurethane, HIPE (see for example PCT patent application WO94/13704), superabsorbent foams and the like, fiber assemblies such as meltblown, spunbond, carded, cellulose webs, fiber beds and the like, porous particles such as clay, zeolites, and the like, geometrically structured materials such as tubes, balloons, channel structures etc. Porous materials might absorb liquids even if they are not hydrophilic. The porosity of the materials is therefore not linked to their affinity for the liquid that might be absorbed.

The term "substantially geometrically saturated" as used herein refers to a member in which at least 90% of the macroscopic void volume of the member are geometrically saturated, preferably at least 95% of the macroscopic void volume of the device are geometrically saturated, more preferably 97% of the macroscopic void volume of the device are geometrically saturated, most preferably 99% of the macroscopic void volume of the device are geometrically saturated.

In one embodiment of the present invention, the absorbent article is a disposable absorbent article such as a diaper, a training pant, a sanitary napkin, an adult incontinence article, or the like. Such an absorbent article may further comprise a liquid pervious topsheet, a liquid impervious backsheet at least partially peripherally joined to the topsheet. The absorbent article may further comprise an absorbent core which may serve as a storage member for the urine. Topsheets, backsheet, and absorbent cores suitable for the present invention are well known in the art. In addition, there are numerous additional features known in the art which can be used in combination with the absorbent article of the present invention such as for example closure mechanisms to attach the absorbent article around the lower torso of the wearer.

What is claimed is:

1. A liquid removal system which comprises an interface device, said interface device comprising a first zone and a second zone and having a porous membrane separating said first zone from said second zone, said second zone being adapted to be connected to a suction source, said porous membrane being capable of maintaining a suction in said second zone without permitting air from said first zone to pass through said membrane into said second zone when said membrane has been wetted with a first liquid; said suction being maintained until said membrane is contacted with a second liquid; and wherein said second liquid upon entering said first zone and contacting said porous membrane is removed from said first zone by said suction in said second zone by passing through said membrane into said second zone said first zone having a user facing surface, said second zone having a back surface, characterized in that said interface device is compressible in the longitudinal direction and/or is compressible in the transverse direction to less than 90 percent of its original dimension in that direction, wherein said second zone comprises a flexible support means and said second zone is enveloped by a flexible, liquid impermeable backsheet, wherein said flexible support means comprises a plurality of substantially incompressible elements, at least a portion of said plurality of substantially incompressible elements being freely movable inside said second zone.

2. A liquid removal system according to claim 1, said user facing surface comprising a urine acquisition zone wherein at least said urine acquisition zone is covered by a soft, compliant topsheet.

3. A liquid removal system according to claim 2 wherein said topsheet is a carded nonwoven web material.

4. A liquid removal system according to claim 3 wherein said carded nonwoven web material is a high bulk nonwoven web material.

5. A liquid removal system according to claim 1 wherein said plurality of substantially incompressible elements comprises elements selected from the group of spheres, Raschig rings, Pearl saddles.

6. A liquid removal system according to claim 1 wherein said flexible liquid impermeable backsheet comprises a layer of nonwoven web material on its outer surface.

7. A liquid removal system according claim 1 wherein said liquid removal system further comprises an external dam disposed onto the user facing surface of said first zone wherein said external dam comprises a liquid impermeable nonwoven barrier cuff.

8. A liquid removal system according to claim 7 wherein said nonwoven barrier cuff is vapor permeable.

* * * * *

UNITED STATES PATENT AND TRADEMARK OFFICE
CERTIFICATE OF CORRECTION

PATENT NO. : 6,932,797 B2
DATED : August 23, 2005
INVENTOR(S) : Mattias Schmidt et al.

It is certified that error appears in the above-identified patent and that said Letters Patent is hereby corrected as shown below:

Column 7,
Line 6, delete "according claim 1" and insert -- according to claim 1 --.

Signed and Sealed this

Seventeenth Day of January, 2006

JON W. DUDAS
*Director of the United States Patent and Trademark Office*